Figure 1:
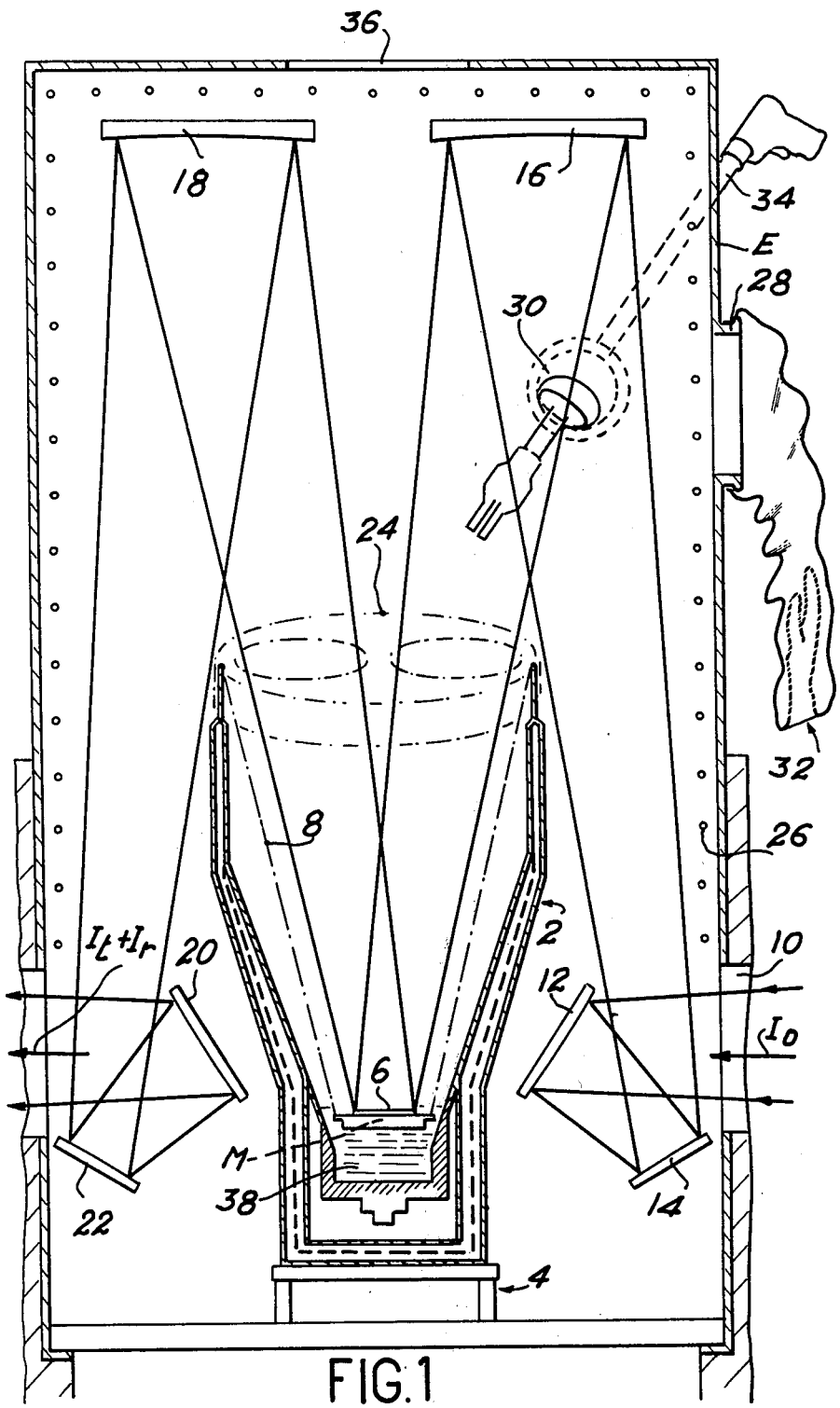

United States Patent [19]

Ceccaldi et al.

[11] 3,979,325

[45] Sept. 7, 1976

[54] WINDOWLESS CRYOSTATIC DEVICE FOR LOW-TEMPERATURE SPECTROMETRY

[75] Inventors: Maurice Ceccaldi, Chatillon; Pierre Roubeau, Palaiseau, both of France

[73] Assignee: Commissariat a l'Energie Atomique, Paris, France

[22] Filed: Apr. 10, 1975

[21] Appl. No.: 566,700

[30] Foreign Application Priority Data

Apr. 22, 1974 France .............................. 74.13951

[52] U.S. Cl. .............................. 250/352; 62/467 R; 250/338; 356/51
[51] Int. Cl.² ........................................... G01J 3/02
[58] Field of Search ........... 250/330, 332, 333, 334, 250/338, 340, 352; 62/132, 268, 467, DIG. 9; 356/51, 36, 38

[56] References Cited
UNITED STATES PATENTS

| | | |
|---|---|---|
| 2,996,893 | 8/1961 | Goodenough et al. ......... 250/352 X |
| 3,025,680 | 3/1962 | DeBrosse et al. ................. 250/352 X |
| 3,899,674 | 8/1975 | Decramer et al. .................. 250/352 |
| 3,906,231 | 9/1975 | Fletcher et al. ...................... 250/338 |

*Primary Examiner*—Archie R. Borchelt
*Attorney, Agent, or Firm*—McNenny, Pearne, Gordon, Gail, Dickinson & Schiller

[57] ABSTRACT

A cryostatic device employed mainly in infrared spectrometry comprises a vertical open-topped vessel having heat-insulating reflecting walls and containing a cryogenic liquid, an outer enclosure surrounding the vessel and provided with at least one opening for establishing a communication between the external atmosphere and a region of the enclosure opposite to the lower portion of the vessel, means for introducing cryogenic liquid into the vessel and means whereby the sample to be studied is maintained in position and cooled by said cryogenic liquid.

9 Claims, 2 Drawing Figures

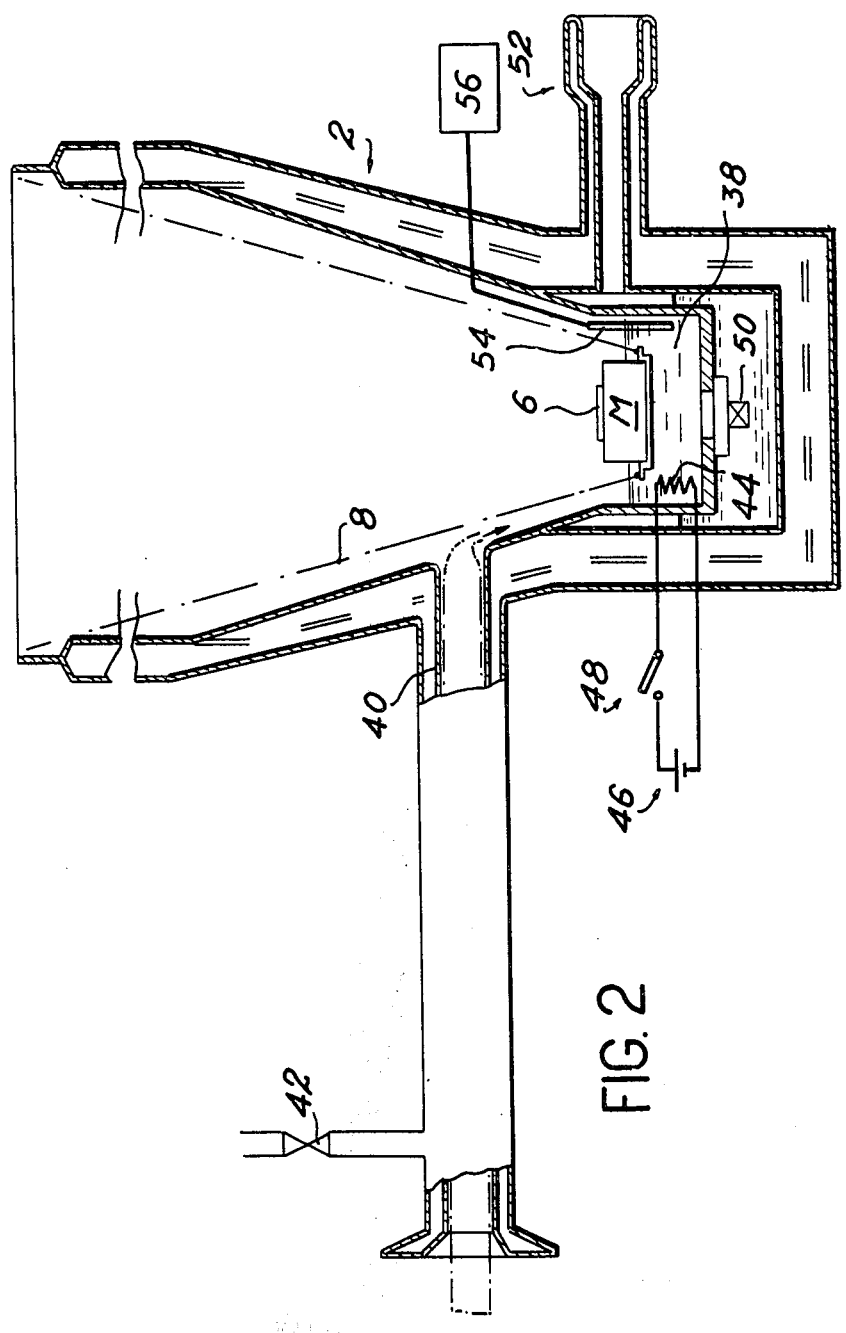

WINDOWLESS CRYOSTATIC DEVICE FOR LOW-TEMPERATURE SPECTROMETRY

This invention relates to a "windowless" cryostatic device for low-temperature spectrometry comprising a vessel in which is placed a sample to be optically analyzed and a bell-type enclosure referred-to as a "bell-chamber".

Three types of cryostats are known to exist at the present time:

the cryostats of the conductivity type in which the heat transfer between the sample and a cooled block takes place by conductivity. The sample and the block must be located within a chamber in which a vacuum has been produced;

the cryostats in which the sample is immersed in a cryostatic liquid; these cryostats have a disadvantage in that they limit the choice of temperatures to the temperatures of utilizable liquids. Moreover, in the case of optical assemblies, it is necessary to have a minimum of two windows such that one window is in contact with the cold liquid and the other window is interposed between the sample and the light beam. This window-type device has a disadvantage in that any temperature build-up at the level of the sample is liable to result in the formation of bubbles in contact with said sample and thus to modify the transmission of light; this effect is important in the infrared range in which the long wavelengths are highly diffracted by obstacles;

the cryostats of the convection type: in these cryostats, the sample is immersed in a cooled gas and the heat transfer takes place by convection; for the optical study of the sample, it is necessary to interpose windows between the sample and the light beam.

Whether assemblies operate on the principle of conductivity or convection, it often proves necessary to restore the device to room temperature in order to change the sample. In optical assemblies, the most suitable cryostat of the so-called convection type nevertheless has the disadvantage of entailing the use of windows which have poor heat conductivity. Even when such windows can be prevented from coming into direct contact with the sample, they are to be avoided in infrared light applications. In fact, windows which are easy to use such as germanium windows have a high refractive index, thereby entailing high reflection of the beam at each interface, even under conditions of normal incidence. A large proportion of the beam is then lost by reflection. Other windows such as those formed of crystallized salt such as sodium chloride are hygroscopic and are consequently damaged when they are employed in free air; moreover, such windows cannot be in contact with certain chemical compounds with which they react chemically.

The present invention relates to a windowless cryostatic device which is primarily applicable to low-temperature spectrometry, said device being designed to ensure low heat losses and so arranged as to ensure that the sample which is readily interchangeable and permits manipulation at any temperature is not in contact with the external atmosphere.

In more precise terms, the cryostatic device in accordance with the invention comprises:

a vertical open-topped vessel having heat-insulating reflecting walls and containing a cryogenic liquid in the bottom portion of said vessel;

a so-called bell-chamber E surrounding the vessel and provided with at least one opening, said opening being such as to establish a communication between the external atmosphere and a region located within the bell-chamber E but outside the vessel and well below the open top extremity of said vessel;

means for maintaining the sample to be studied in a position such as to ensure that said sample is cooled by the cryogenic liquid;

means for introducing the cryogenic liquid into the vessel.

In one preferential embodiment of the invention, the device comprises means whereby the level of cryogenic liquid within the vessel is measured and maintained constant. A known device which can be employed by way of example consists of an immersed thermometer tube whose resistance is dependent on the temperature; the supply of liquid can be controlled so as to maintain the resistance of the thermometer tube at a constant value.

The vapor produced by the cryogenic liquid forms a heat-insulating barrier between the atmosphere at room temperature and the sample which is immersed in or in the vicinity of the liquid at low temperature. The vertical vessel has a substantially cylindrical shape and the liquid is placed at the bottom of the cryostat. The vertical temperature gradient results in a gas density gradient within the vessel and this prevents any convection.

The infrared light beam for example traverses the sample twice after reflection from the mirror M and is directed to a photo-receiver. By comparing the incident light and the transmitted light, the absorption spectrum of the sample is obtained and this makes it possible to determine the composition of the sample and even the structure of this latter if so required. Similarly, a reflection spectrum can be obtained in the event that the absorption capacity of the substance is too high.

In a preferential embodiment of the invention, the sample is placed on a mirror M which is either in contact with the surface of the liquid or completely immersed in the cryogenic liquid together with the sample; in spectrometric applications, means consisting of mirrors are employed for directing a light beam towards the sample and collecting the light transmitted by the mirror-sample assembly.

The vapor produced by evaporation of the cryogenic liquid is removed from the cryostat and discharged to the external atmosphere through openings formed in the bell-type enclosure or chamber. The pressure drop on the path of the vapor within the cryostat between the liquid and the openings formed in the bell-chamber is of sufficient value to prevent gases from being admitted into the cryostat from the external atmosphere. Said pressure drop is produced essentially by the baffle system constituted by the lateral wall of the cryostatic vessel and the opening formed in the bell-chamber. In the case of gases such as argon or nitrogen, it will only be necessary to subject the atmosphere of the vessel and of the bell-chamber to an initial drying operation and also to remove the condensable products such as carbon dioxide gas by sweeping with a dry gas, for example.

In the case of light fluids such as helium or hydrogen, the gas which evaporates is lighter than air. It is accordingly necessary in such cases to remove the air from the vessel and from the bell-chamber by sweeping with the same gas for example, this operation being carried out prior to introduction of the cryogenic liquid. Moreover, the flow rate of helium or more generally of the evaporated light gas must be sufficient to force back the external atmosphere during operation. It may prove necessary to increase the evolution of gas by artificial means such as local heating of the liquid or injection of gaseous helium.

In one preferential embodiment of the invention, the bell-chamber E is lined with a reflecting screen placed in the immediate vicinity of the internal surface of said bell-chamber E, said screen being provided with openings located opposite to the openings formed in said bell-chamber and with viewing and handling ports. Said reflecting screen serves to reduce the radiation temperature of the bell-chamber.

In one embodiment of the invention, the top end of the vessel is fitted with a detachable reflecting lid pierced by two openings, the incident light beam and the light beam reflected from the mirror M being intended to pass through said openings. Said detachable lid serves to insulate the vessel with respect to the bell-chamber.

In one embodiment of the invention, the cryostat comprises an inlet tube which serves to supply the cryogenic liquid and communicates with the bottom portion of the vessel, a suspension carriage for supporting the mirror M which is attached to the top rim of the vessel, a double-walled interstitial vacuum enclosure constituting the internal and external walls of the vessel, pumping means connected to the space formed between the two vessel walls, and a calibrated leak located between the bottom portion of the vessel and a second pumping duct which permits expansion of the cryogenic liquid within a false bottom of the vessel in order to cool said liquid.

The calibrated leak serves to cause expansion of the liquid gas such as helium for example in order to cool and to produce a further reduction of the sample temperature. For example, helium transition to the superfluid state makes it possible to attain very low temperatures (if necessary as low as 2.17°K).

In a preferential embodiment of the invention, the bell-chamber E has a beam entrance opening and a beam exit opening which are located between the bottom of the bell-chamber and the top end of the vessel, a system of mirrors being intended to reflect the light beam between the beam entrance and beam exit openings and the sample, two ports located in the lateral portion of the bell-chamber E, one port being fitted with a rubber glove and the other port with a ball/tong unit and a transparent viewing port located on the top portion of the bell-chamber E.

The bell-chamber E directs the vapors of the cryogenic liquid towards the exterior while preventing the admission of ambient gas. The openings have a shape such that access can be gained to the cryogenic region without encountering walls. This path is employed for the purpose of introducing samples and collecting the light reflected and transmitted by this latter.

Further properties and advantages of the invention will become more readily apparent from the following description of examples of construction which are given by way of explanation without any limitation being implied, reference being made to the accompanying drawings, wherein:

FIG. 1 is a general diagram of the cryostat;
FIG. 2 is a detail drawing of the cryostat.

The device in accordance with the invention as shown in the diagram of FIG. 1 comprises a vessel 2 whose base rests on a support 4 which is secured to the bottom wall of the enclosure E. The sample 6 is placed on the mirror M, said mirror being located in the vicinity of the bottom of the vessel 2 by means of a suspension carriage 8 which is attached to the top rim of the vessel 2.

The light beam $I_0$ passes through the opening 10, is reflected from the mirrors 12, 14 and 16 and then impinges on the sample 6. The light beams which are reflected and transmitted (after two traversals through the sample 6) are collected by the mirrors 18, 20 and 22 and then pass out of the enclosure or bell-chamber E.

In a preferential embodiment of the invention, the double-walled vessel 2 is fitted with a lid 24 pierced by two openings through which the incident and reflected light beams pass. The bell-chamber E is lined with a reflecting screen 26 and provided with two ports 28 and 30; the port 28 is fitted with a glove finger 32 and the port 30 is fitted with a ball/tong unit 34. The bell-chamber E is also provided with a transparent port 36 for viewing the bottom of the vessel 2. The bottom of the vessel 2 is filled with a liquid as designated by the reference 38, for example. The height of the wall of the vessel 2, the mirrors such as those designated by the references 12, 14, 20, 22 and the positions of the openings 10 are such that the gases which escape from the cryostat to the exterior experience a pressure drop of sufficiently high value to permit an admission of air.

FIG. 2 is a sectional view of the cryostat in accordance with the invention. The double-walled vessel 2 is provided with an inlet tube 40 through which the liquid (such as helium for example) is introduced. The vacuum for insulating the vessel is produced by a pump (not shown in FIG. 2) which is connected through the valve 42. The bottom of the vessel 2 is filled with liquid 38 and the mirror M which supports the sample 6 is immersed in said liquid. In a variant of the invention, a resistance element 44 which is heated by means of a dry-cell unit 46 and a switch 48 serves to vaporize the liquid within the cryostat at a higher rate. An adjustable valve 50 serves to expand the liquid 38 in order to cool this latter by adiabatic expansion. The formed gas escapes through the tube 52 which is connected to a pumping system (not shown). A thermometer tube 55 of known type whose resistance is measured by means of an electronic device 56 serves to measure and maintain constant the level of liquid within the vessel.

What we claim is:
1. A windowless cryostatic device for low-temperature spectrometry and primarily employed in infrared spectrometry, wherein said device comprises:
   a vertically oriented vessel having an open top, heat-insulating walls and a bottom portion capable of containing a cryogenic liquid;
   a cryogenic liquid contained in said bottom portion of said vessel;
   a bell-shaped housing encapsulating the vessel, said housing defining an interior chamber containing said vessel, said housing provided with at least one aperture, said aperture being such as to establish an area of communication between a point external to said housing and said interior chamber, said area of communication being a spaced distance below the open top of said vessel;

support means for maintaining a sample to be studied in a position above said cryogenic liquid such as to ensure that said sample is cooled by said support means, said support means being cooled by the cryogenic liquid;

means for introducing the cryogenic liquid into the vessel.

2. A device according to claim 1, wherein said device includes means whereby the level of cryogenic liquid within the vessel is measured and maintained constant.

3. A device according to claim 1 wherein said support means for maintaining a sample includes a horizontal first mirror on which is placed a sample whose absorption and reflection spectrum is to be recorded, a portion of said mirror being in contact with the cryogenic liquid, said device further comprising means for directing a light beam towards a sample placed on said first mirror through the open top of said vessel whereby said beam is reflected from said first mirror so as to emerge through the open top of said vessel.

4. A cryostatic device according to claim 1 wherein said interior chamber of said bell-shaped housing is lined with a reflecting screen.

5. A cryostatic device according to claim 1 wherein the open top of the vessel is fitted with a detachable reflecting lid provided with at least one opening through which a light beam can pass.

6. A cryostatic device according to claim 3 wherein the vessel includes an inlet tube which serves to supply the cryogenic liquid and communicates with the bottom portion of the vessel, a suspension carriage attached to the top of the vessel for supporting the first mirror, a double-walled interstitial vacuum enclosure constituting the heat insulating walls of the vessel; pumping means connected to said double walled interstitial vacuum enclosure and a duct and a calibrated leak located between the bottom portion of the vessel and said duct said calibrated leak permitting expansion of a portion of the cryogenic liquid within said duct.

7. A cryostatic device according to claim 3 wherein said device includes means for heating and evaporating the cryogenic liquid.

8. A windowless cryostatic device according to claim 3 wherein said bell-shaped housing includes a beam entrance aperture and a beam exit aperture which are each located substantially below the open top of the vessel;

said interior chamber containing a plurality of mirrors including said horizontal first mirror for reflecting a light beam between the beam entrance aperture, a sample and the beam exit aperture;

two ports located on said housing and fitted respectively with a rubber glove and with a ball/tong unit:

a transparent viewing port located on the top portion of said housing.

9. A windowless cryostatic device for low-temperature spectrometry primarily employed in infrared spectrometry comprising:

a vertically oriented vessel having an open top, heat-insulating walls, and a bottom portion capable of containing a cryogenic liquid;

a metallic piece having a light reflecting generally flat top located a predetermined distance above said bottom portion of said vessel for supporting and cooling a sample to be spectrometrically analyzed;

a bell-shaped housing generally encapsulating said vessel, said housing defining an interior chamber containing said vessel, said bell-shaped housing having at least one aperture establishing an area of communication between said interior chamber and a point external to said bell-shaped housing, said area of communication being substantially below said open top;

means for introducing cryogenic liquid into the bottom portion of said vessel.

* * * * *